United States Patent [19]
Jayaraman

[11] Patent Number: 5,902,299
[45] Date of Patent: May 11, 1999

[54] CRYOTHERAPY METHOD FOR REDUCING TISSUE INJURY AFTER BALLOON ANGIOPLASTY OR STENT IMPLANTATION

[76] Inventor: Swaminathan Jayaraman, 3415 Misty Meadow Dr., Dallas, Tex. 75287

[21] Appl. No.: 08/902,020

[22] Filed: Jul. 29, 1997

[51] Int. Cl.$^6$ .................................................. A61B 17/36
[52] U.S. Cl. ........................ 606/20; 606/22; 604/101
[58] Field of Search .................. 606/20–26; 604/113, 604/53, 101

[56] References Cited

U.S. PATENT DOCUMENTS

| | | |
|---|---|---|
| 5,059,166 | 10/1991 | Fischell et al. |
| 5,092,841 | 3/1992 | Spears . |
| 5,140,012 | 8/1992 | McGovern et al. |
| 5,150,717 | 9/1992 | Rosen et al. |
| 5,176,674 | 1/1993 | Hofmann . |
| 5,213,561 | 5/1993 | Weinstein et al. |
| 5,242,397 | 9/1993 | Barath et al. |
| 5,284,869 | 2/1994 | Bisaccia et al. |
| 5,298,018 | 3/1994 | Narciso, Jr. |
| 5,370,608 | 12/1994 | Sahota et al. |
| 5,417,653 | 5/1995 | Sahota et al. |
| 5,422,362 | 6/1995 | Vincent et al. |
| 5,575,811 | 11/1996 | Reid et al. |

*Primary Examiner*—Beverly M. Flanagan
*Assistant Examiner*—Roy Gibson
*Attorney, Agent, or Firm*—Larson & Larson, P.A.; James E. Larson

[57] ABSTRACT

A cryotherapy method for reducing tissue injury after balloon angioplasty or stent implantation contemplates use of a well insulated, low profile catheter designed to transport a low temperature medium such as gas, fluid or a mixture thereof at a particular temperature over a guide wire to the site of a lesion. The lesion may or may not have undergone previous procedure for balloon angioplasty or stent implantation. The cryo-medium is introduced from a well insulated storage chamber having a small nozzle to which a conduit may be attached to allow conveyance of the fluid to a point of use. A handheld valve is incorporated into the conduit to allow the surgeon to closely control the flow of the cryo-medium to the point of use. The conduit extends downstream of the valve and is fluidly connected to the catheter that is positioned at the point of the lesion in the body. If desired, antibiotics, anticoagulants, antiproliferative agents, gene materials, etc. may also be dispersed along with the cryo-medium intraluminally. Such additional substances may be mixed with the cryo-medium in the storage chamber before introduction into the catheter or concurrently with introduction into the catheter. Several alternative catheter structures are contemplated in accordance with the teachings of the present invention.

11 Claims, 4 Drawing Sheets

CRYOTHERAPY METHOD FOR REDUCING TISSUE INJURY AFTER BALLOON ANGIOPLASTY OR STENT IMPLANTATION

BACKGROUND OF THE INVENTION

The present invention relates to a cryotherapy method for reducing tissue injury after balloon angioplasty or stent implantation. One of the well known and well documented causes of failure of angioplasty (use of a balloon inflated within an artery to compress occluding materials against the inner arterial wall) or stent implantation is the mechanism of restenosis. Restenosis is evidenced when the artery re-occludes due to tissue ingrowth and/or elastic recoil of the arterial wall at the site of the prior occlusion.

After a balloon angioplasty procedure or stent implantation procedure has been completed, the arterial wall often exhibits damage or inflammation due to the required use of force from inflation of a balloon catheter against the cellular layers of the arterial wall. This ingrowth phenomenon, namely, restenosis, affects the long term success of balloon angioplasties and stent implantations. In the prior art, cryotherapy is a known technique for preserving tissues at reduced temperatures for short periods of time. Cryotherapy has been decisively shown to be effective in tissue preservations maintenance of tissue function and facilitation of tissue healing processes. Some of the well-defined applications of cryotherapy include the following:

(1) Tissues collected from bovine, pigs and sheep are preserved at reduced temperature so that the elastic membranes or elastin present in the tissues is protected for subsequent applications. Without the use of such temperature reduction, the tissues dry out and lose their original mechanicals, physical and chemical properties.

(2) During open heart surgery, when the heart is opened to either replace a valve or an underlying diseased coronary artery, the myocardium or the tissues surrounding the heart are exposed to reduced temperature by dipping them in ice or sub-cooled water while the surgery is underway to preserve them.

(3) During open heart surgery, when the aorta is cross-clamped and blood from the heart is directed into a heart-lung machine, the blood is mixed with cold cardioplegia solution to preserve the cells and other essential components in the blood, an especially critical procedure where surgery is lengthy.

(4) Bovine and other homograft valves that have been preserved in cryo-based solutions and reduced temperature environment have been shown to have superior performance during long term follow-up studies when compared with mechanical bileaflet or single leaflet valves.

(5) In many pain management therapeutic situations, the area or region of acute pain is exposed to reduced temperature fluids or "cold packs" to reduce nerve damage and relieve pain.

The prior art teaches several techniques designed to reduce or eliminate the onset of restenosis. However, Applicant is unaware of any such technique that involves the use of application of reduced temperature within an artery.

One of the most common causes of recurrence of luminal narrowing after balloon angioplasty or stent implantation is the ingrowth of tissue at the site of the previous blockage. When a balloon is inflated at the site of a lesion where the artery is occluded, the lesion is mechanically pushed up by force acting thereon due to inflation of the balloon. Pathology of experiments in pigs and sheep reveals that the balloon inflation causes endothelial injury as well as tissue dislodgement at the site of the lesion. Such an injury is characterized by inner lumen wall cracks that are filled up with blood and some thrombis (clotting material). These cracks may infiltrate into the second and third layers of the vessel wall that are termed adventitia and media primarily composed of collagen, smooth muscle cells and elastic cells that contribute to the compliance of the artery.

When these layers are disrupted due to balloon inflation or stent implantation, compliance response is lost. This results in proliferation of cells as a function of time. Although the proliferation starts immediately after the injury to the arterial wall, maximum proliferation may be observed 6 to 18 months after the initial injury.

Applicant is aware of the following prior art:

U.S. Pat. No. 5,059,166 to Fischell et al. discloses a technique for reducing the onset of intimal hyperplasia which technique involves the use of irradiation from a radioisotope.

U.S. Pat. No. 5,213,561 to Weinstein et al. also discloses the use of radioactive material to reduce the incidence of restenosis.

U.S. Pat. No. 5,092,841 to Spears discloses the bonding of a bioprotective material to the arterial wall where angioplasty has been conducted.

U.S. Pat. No. 5,140,012 to McGovern et al. discloses a method for preventing onset of restenosis after angioplasty which involves administration of pravastatin in combination with an ACE inhibitor.

U.S. Pat. No. 5,242,397 to Barath et al. discloses prevention or reduction of the incidence of late restenosis through the administration of protein kinase C and tyrosine protein kinase inhibitors.

U.S. Pat. No. 5,284,869 to Bisaccia et al. discloses a method for preventing restenosis following angioplasty that includes the use of a photophoresis treatment method.

U.S. Pat. No. 5,298,018 to Narciso, Jr. discloses administration of a photosensitizer prior to surgical or interventional procedure which is then re-administered after the procedure to maintain the photosensitizer concentration level in the atheromatous plaque and smooth muscle cells in the vicinity of the lesion for a period of about 5–18 days.

U.S. Pat. No. 5,422,362 to Vincent et al. discloses administration of a green porphyrin to the location of vascular intervention to inhibit the onset of restenosis.

None of the patents discussed above teaches, discloses or suggests the use of a cryo-technique to reduce the onset of restenosis after a balloon angioplasty or stent implantation.

Further, Applicant is aware of an article titled "THE ROLE OF CRYOTHERAPY FOR AIRWAY COMPLICATIONS AFTER LUNG AND HEART-LUNG TRANSPLANTATION" by Maiwand et al. The article discusses the use of cryotherapy in causing cell lysis of granulation tissue and speculates that such a technique may therefore be effective after lung transplantation for difficult airway problems. This article fails to teach or suggest the use of cryotherapy techniques for reduction of the onset of restenosis within the arterial wall of a patient on whom balloon angioplasty or stent implantation has been completed.

SUMMARY OF THE INVENTION

The present invention relates to a cryotherapy method for reducing tissue injury after balloon angioplasty or stent implantation. The present invention includes the following interrelated objects, aspects and features:

(1) The present invention contemplates a well insulated, low profile catheter designed to transport a medium such as gas, fluid or a mixture thereof at a particular temperature over a guide wire to the site of a lesion. The lesion may or may not have undergone previous procedure for balloon angioplasty or stent implantation.

(2) The medium is introduced in the following preferred way: air is mixed with FREON® or helium and is compressed in a chamber to very low temperature between 14° C. and −10° C. The medium also can be water, water mixed with saline, water mixed with a fluorinated hydrocarbon used to lower temperature. From the compression chamber, the cooled fluid is conveyed to a well insulated storage chamber having a small nozzle to which a conduit may be attached to allow conveyance of the fluid to a point of use. A handheld valve is incorporated into the conduit to allow the surgeon to closely control the flow of the cryo-medium to the point of use. The conduit extends downstream of the valve and is fluidly connected to the catheter that is positioned at the point of the lesion in the body.

(3) Additionally, antibiotics, anticoagulants, antiproliferative agents, gene materials, etc. may also be dispersed along with the cryo-medium intraluminally. Such additional substances may be mixed with the cryo-medium in the storage chamber before introduction into the catheter or concurrently with introduction into the catheter.

(4) These additional substances may also be introduced prior to introduction of the cryo-medium or thereafter.

(5) The procedure for introduction of the cryo-medium and other substance(s) can be applied to all intraluminal, intercranial and endovascular procedures regardless of the size of the lumen of the artery or the vein and regardless of the site on the body where it is located.

(6) Several alternative catheter structures are contemplated in accordance with the teachings of the present invention. These catheter structures are the following:

(a) The catheter may be provided with two lumens, one for introduction over a guide wire and a second lumen having a plurality of holes at the distal end thereof that act as the point of delivery for the cryo-medium and other substance(s). These holes may be provided over an area prescribed based upon the length of the lesion and the diameter of the artery involved.

(b) The catheter may have a triple lumen where one lumen is provided for the guide wire, the second lumen is provided for balloon inflation to center the catheter, and the third lumen is used for delivery of the cryo-medium and other substance(s).

(c) The catheter may have four lumens where three of the lumens perform the functions described in subparagraph (b) above, and the fourth lumen provides an additional balloon so that there is one balloon upstream of the lesion site and one balloon downstream of the lesion site to isolate the lesion site on both sides with delivery of the cryo-medium occurring therebetween.

(d) If desired, the mechanism for delivery of the cryomedium can comprise a balloon having pores formed in a second layer thereof.

(e) Alternatively, the delivery mechanism can comprise a simple shaft having a distal tip with an opening or holes thereon that may be closed while the catheter is being introduced into the body but which may be opened by withdrawing a sheath or a similar protective mechanism.

(f) All the delivery mechanisms can incorporate a sensor or thermistor or similar temperature recording device on the tip or body of the lumen which will be indicated on a temperature readout.

Accordingly, it is a first object of the present invention to provide a cryotherapy method for reducing tissue injury and/or restenosis after balloon angioplasty or stent implantation. The procedure is applicable to surgical, interventional, endovascular or percutaneous procedures.

It is a further object of the present invention to provide such a method wherein a cryo-medium is created and stored within a container for later delivery via a catheter.

It is a still further object of the present invention to provide such a method wherein other substances (s) may be supplied at the area of a lesion along with a cryo-medium.

It is a yet further object of the present invention to provide such a method wherein a catheter is provided having anywhere from one to four lumens provided to guide the catheter to its place of locations, allow inflation of one or more balloons to maintain the catheter end at a desired location, and a plurality of holes to allow dispensing of the cryo-medium.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
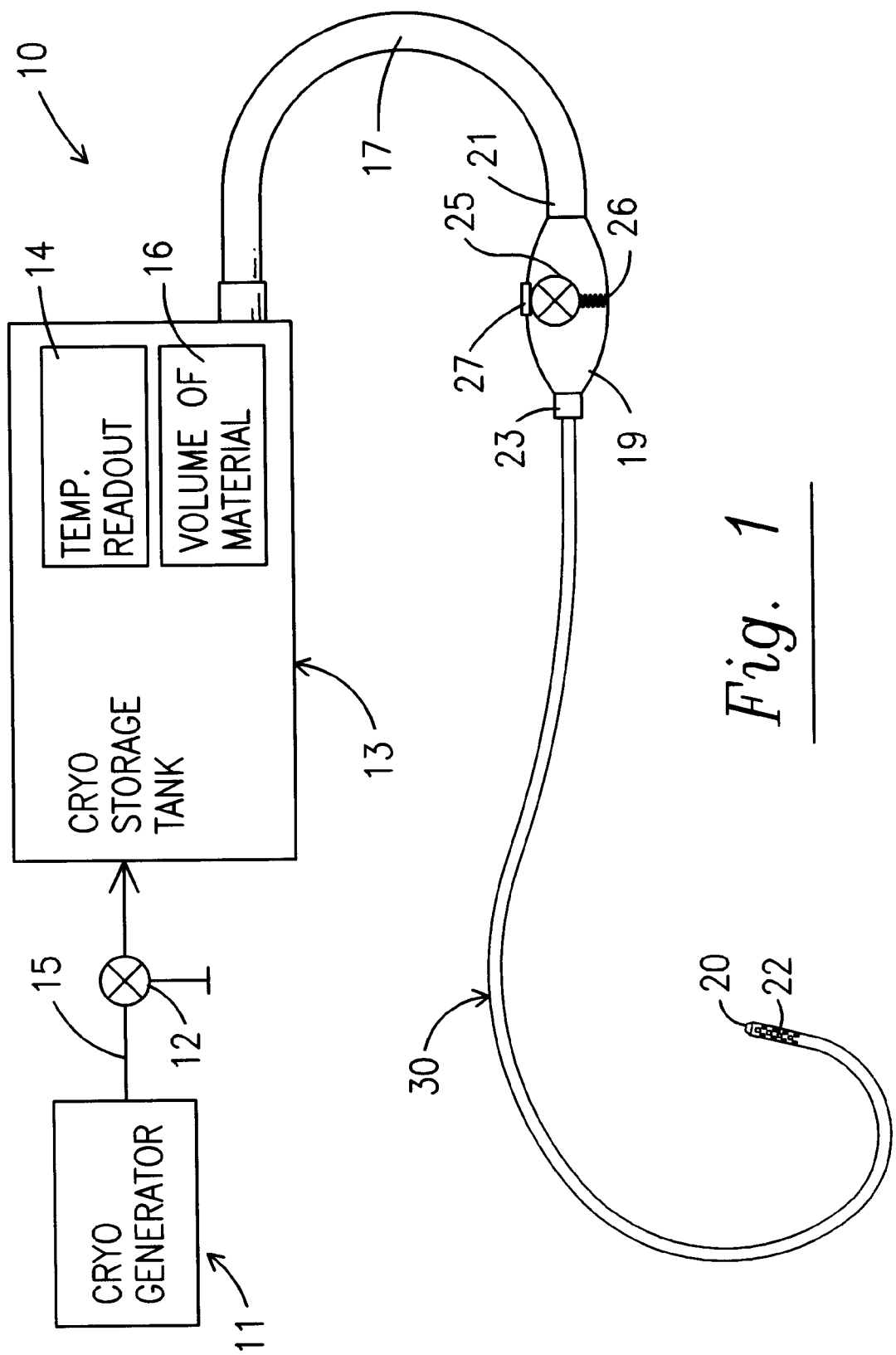
FIG. 1 shows a schematic representation of the overall system of the present invention.

With reference, first, to FIG. 1, the overall system of the present invention is generally designated by the reference numeral 10 and is seen to include a cryo-generator 11, a cryo-storage tank 13, a conduit 15 interconnecting the cryo-generator 11 with the cryo-storage tank 13, and an outlet conduit 17 allowing flow of cryo-medium from the storage tank 13 to a handheld controller 19 consisting of an inlet port 21, an outlet port 23, and a valve 25 having a valve actuator 27 that may be manipulated by the user to allow metering of a flow path through the valve 25 to allow control of flow rate of cryo-medium into the catheter 30. The valve 25 may be of any desired type including one having a spring 26 biasing the valve head to a position of closure so that when the actuator 27 is released, the valve 25 is restored to the closed position. Any suitable valve that will firmly and repeatedly seat to block flow in the contemplated environment, to-wit, that of a cryo-medium having a temperature between 14° C. and −10°C. may be employed. Such valves are well known to those skilled in the art.

Figure 2:
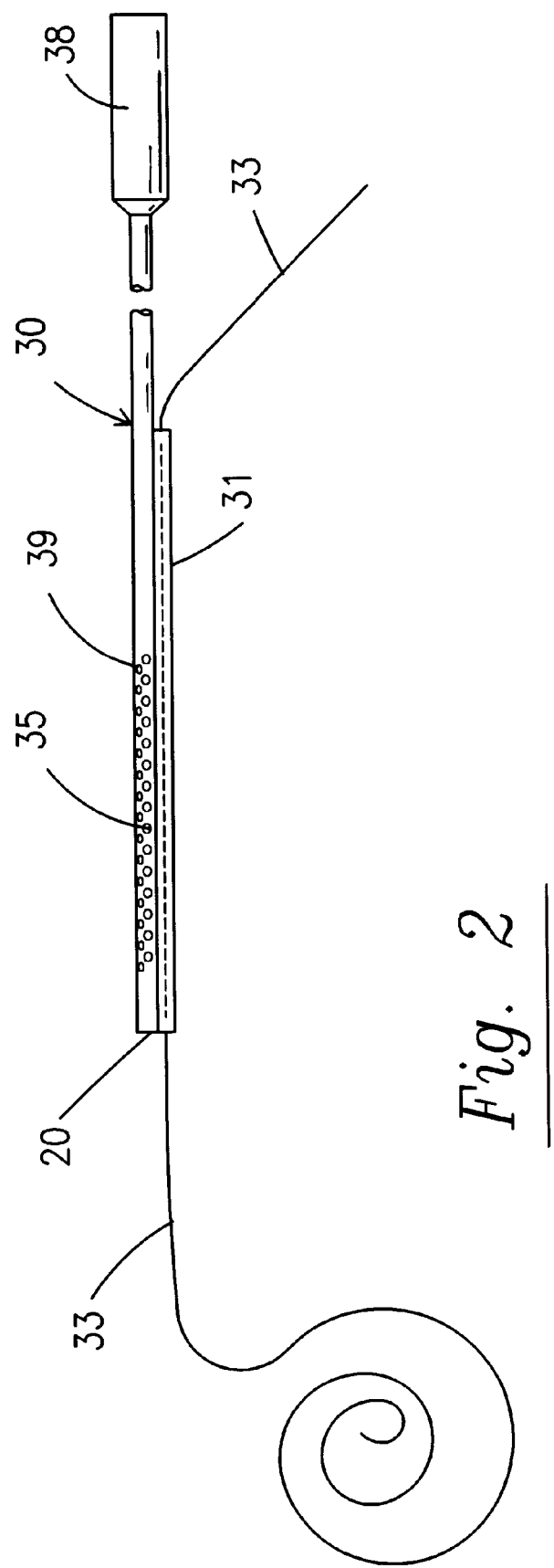
FIG. 2 shows a longitudinal cross-sectional view through a first embodiment of catheter including two lumens.

As further seen in FIG. 1, the storage tank includes two gauges, a temperature read-out gauge 14 and a volume or pressure display 16. The temperature gauge 14 records temperature at the sensor 20. Holes 22 disperse the cryo-medium. The volume display 16 may display rate of flow of cryo-medium in any manner well known to those skilled in the art. For example, the flow path of cryo-medium may include a conduit with a restricted orifice and with sensor lines just upstream and downstream of the restricted orifice. The pressure differential on either side of the restricted orifice relates to flow rate in a manner well known to those skilled in the art. FIG. 2 shows more details of the catheter 30 also shown in FIG. 1 With reference to FIG. 2, the catheter 30 includes two lumens, a first lumen 31 provided for insertion therethrough of a guide wire 33 designed to guide movement of the catheter 30 to its desired location. The second lumen 35 includes a plurality of ports 39 in a prescribed pattern and extent designed to dispense cryo-medium to the desired location for the reasons explained herein. The catheter 30 also includes a hub 38 designed to be coupled to a hand held monitor.

Figure 3:
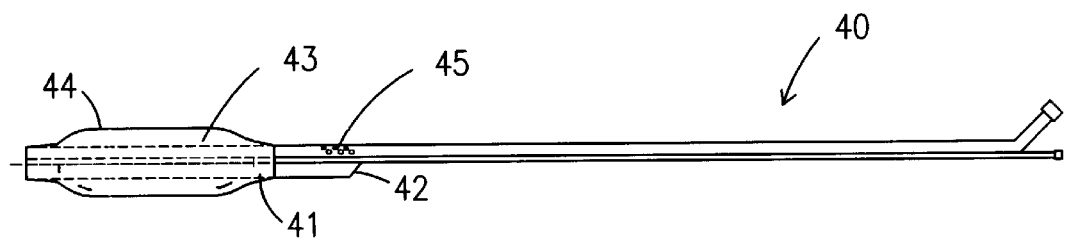
FIG. 3 shows a further side view, partially in cross-section, of the embodiment illustrated in FIG. 2.
Figure 4:
FIG. 4 shows a second embodiment of catheter including three lumens.

FIGS. 3 and 4 show a second embodiment of catheter generally designated by the reference numeral 40 and including three lumens. One lumen 41 includes a port 42 designed to allow insertion of a guide wire (not shown). A second lumen 43 is provided to allow inflation of the balloon 44. A third lumen includes a plurality of holes 45 therein in a prescribed pattern and extent designed to allow dispensing of cryo-medium at the desired site.

Figure 5:
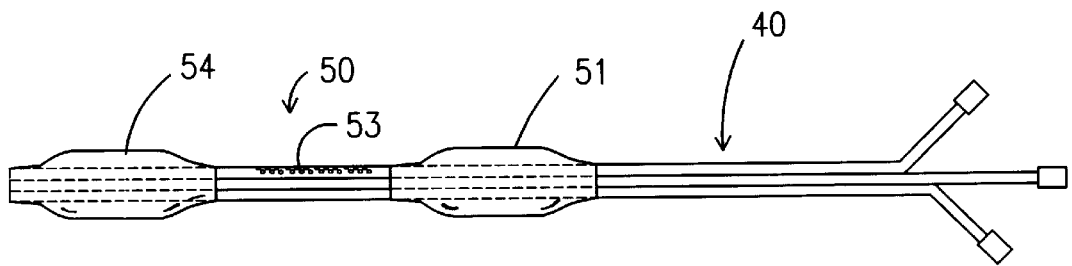
FIG. 5 shows a third embodiment of catheter including the use of four lumens.

With reference to FIG. 5, a further embodiment of catheter designated by the reference numeral 50 includes all of the features of the catheter 40 but with the addition of a further balloon 51 upstream of the site where cryo-medium is to be dispensed. The openings 53, corresponding to the openings 45 in the catheter 40, are provided in a prescribed pattern and extent and the balloon 54 corresponds to the balloon 44 so that the balloons 51 and 54 define, therebetween, an isolated region where the cryo-medium is to be dispensed.

Figure 6:
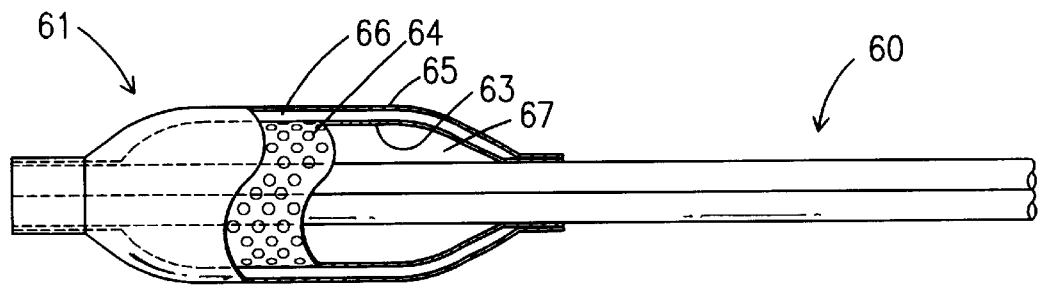
FIG. 6 shows a fourth embodiment of catheter including a two layered balloon having an inner layer with pores to deliver cryo-medium.

FIG. 6 shows a catheter 60 that includes a balloon 61 having an inner layer 63 and an outer layer 65, with the inner layer 63 including openings 64 therethrough. The cryo-medium may be directed into the space 66 between the inner layer 63 and the outer layer 65 so that the cryo-medium may be dispensed within the chamber 67. In this embodiment, dispensing of the cryo-medium within the chamber 67 eliminates direct contact between the cryo-medium and the arterial wall. However, through heat exchange through the inner layer 63 and the outer layer 65 the effect is the same, namely, cooling of the tissues in a desired manner.

Figure 7:
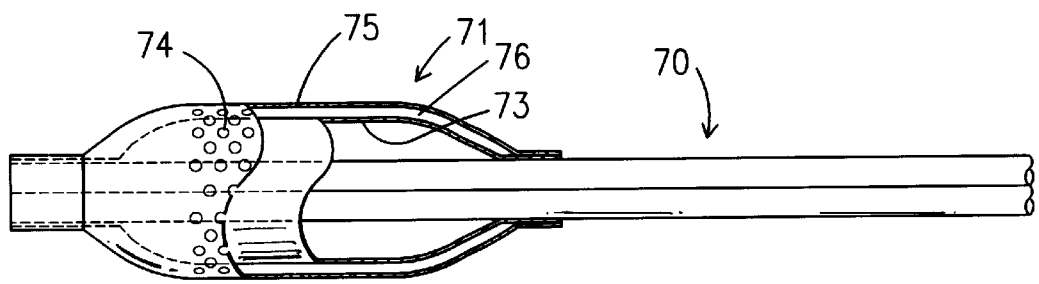
FIG. 7 shows a fifth embodiment of catheter having a two layered balloon with the outer layer having pores to deliver cryo-medium.

FIG. 7 shows a catheter 70 having a balloon 71 with an inner layer 73 and an outer layer 75. Openings 74 are formed in the outer layer and cryo-medium may be directed between the layers 73 and 75 in the space 76 defined therebetween to allow cryo-medium to be dispensed therethrough. In this embodiment, as contrasted to the catheter 60 illustrated in FIG. 6, the cryo-medium directly contacts the arterial wall.

Figure 8:
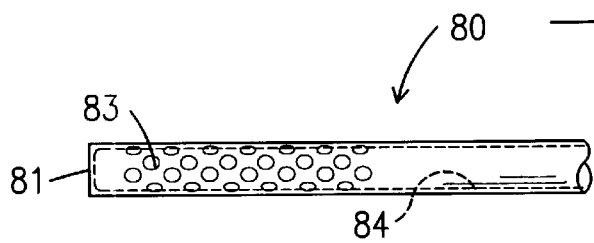
FIG. 8 shows a sixth embodiment of catheter devoid of a balloon but having a series of holes to deliver cryo-medium.
Figure 9:
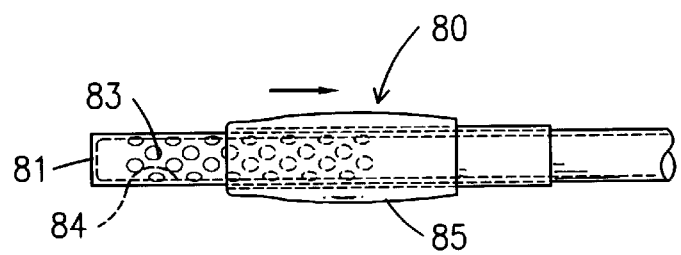
FIG. 9 shows the catheter of FIG. 8 with a flexible sheath covering the delivery holes, which sheath may be withdrawn to expose the holes and allow cryo-medium delivery.

FIG. 8 shows a catheter 80 that is devoid of a balloon but includes a distal end 81 that is closed. On the peripheral walls adjacent the distal end 81 of the catheter 80, a multiplicity of holes 83 are formed in a desired pattern and extent to allow dispensing of cryo-medium through the interior passageway 84 of the catheter 80 and to the location of the desired site of application thereof. In FIG. 9, the catheter 80 is seen to be provided with a flexible, resilient sheath 85 that covers the openings 83 to preclude flow of cryo-medium. The sheath 85 may be withdrawn from covering the openings 83 in a manner well known to those skilled in the art to allow dispensing of cryo-medium, as desired. As explained above, in order to fill the storage tank 13 with cryo-medium, the cryo-generator comprises a compression chamber where air is mixed with FREON® or helium and is compressed until the temperature falls between the range of 14° C. to −10° C. Alternatively, water can be mixed with a fluorocarbon used to lower temperature. Thereafter, the cryo-medium is conveyed through the conduit 15 by opening of the valve 12 to the storage tank 13 which may be well insulated in a manner well known to those skilled in the art to allow the temperature of the cryo-medium to be maintained substantially constant. The cryo-medium is conveyed in the conduit 17 to the handheld controller 19 which includes the valve 25 and actuator 27. When the operator so desires, the desired catheter, one of the catheters described hereinabove with reference to FIGS. 2–9, may be affixed to the outlet port 23 of the handheld controller 19 and the operator can operate the actuator 27 to allow a variety of degrees of opening of the valve 25 to allow flow of cryo-medium through the catheter and to the desired location.

If desired, the cryo-medium may be mixed with other substance or substances such as, for example, antibiotics, anticoagulants, antiproliferative agents, gene matter, etc. that may be disbursed at the desired site along with the cryo-medium intraluminally. These substance(s) may be mixed with the cryo-medium in the cryo-generator 11, in the storage tank 13 or downstream of the handheld controller 19 within the catheter.

As such, an invention has been disclosed in terms of preferred embodiments that fulfill each and every one of the objects of the invention as set forth hereinabove and provide a new and useful cryotherapy technique for reducing tissue injury after balloon angioplasty or stent implantation of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. A method of reducing tissue injury, proliferation and restenosis within a cardiovascular system after a surgical procedure, an interventional, endovascular or percutaneous procedure at a site therein, including the steps of:

a) providing a quantity of a cryo-medium maintained at a temperature below 14° C. in a storage container;

b) fluidly connecting said storage container with a catheter having at least two lumens;

c) inserting said catheter within a cardiovascular system and conveying said catheter to said site with a guide wire within a first lumen;

d) controllably dispensing fluid or gaseous medium from said storage container through a second lumen within said catheter, the second lumen having a plurality of holes at a distal end to deliver the cryo-medium into a cardiovascular system at said site;

(e) providing an inflatable balloon for securing the catheter at the site the balloon having an outer impervious wall and an inner wall with holes therein; and (f) conveying the fluid or gaseous medium between the outer and inner wall and in through the holes.

2. The method of claim 1, wherein said providing step includes the step of maintaining said cryo-medium at a temperature between 14° C. and −10° C.

3. The method of claim 1, wherein said fluidly connecting step includes the step of interposing a valve between said storage container and catheter.

4. The method of claim 1, wherein said inserting step further includes the step opening an orifice in a cardiovascular system.

5. The method of claim 3, wherein said dispensing step includes the step of controllably operating said valve.

6. The method of claim 1, wherein said catheter has two spaced balloons, inflatable upstream and downstream of said site.

7. The method of claim 1, wherein said catheter has an inner passageway with a closed distal end and a peripheral wall with holes therein, said method including the step of dispensing said fluid medium through said holes.

8. A method of reducing tissue injury within a cardiovascular system after a surgical procedure, an interventional, endovascular or percutaneous procedure at a site therein, including the steps of:

a) providing a quantity of a cryo-fluid medium maintained in a storage container at a temperature between 14°C. and −10° C.

b) fluidly connecting said storage container with a catheter via a control valve;

c) inserting said catheter having at least two lumens within a cardiovascular system and conveying said catheter to said site while guiding with a guide wire within a first lumen;

d) controllably dispensing fluid medium from said storage container through a second lumen in said catheter by operating said control valve, the lumen having a plurality of holes at a distal end to deliver the cry-medium into a cardiovascular system at said site;

e) providing an inflatable balloon having an outer impervious wall and an inner wall with holes, therein; and f) conveying the fluid between the outer and inner walls and in through the holes.

9. The method of claim 8, wherein said inserting step further includes the step opening an orifice in a cardiovascular system.

10. The method of claim 8, wherein said catheter has two spaced balloons, inflatable upstream and downstream of said site.

11. The method of claim 8, wherein the second lumen in said catheter has an inner passageway with a closed distal end and a peripheral wall with holes therein, said method including the step of dispensing said fluid medium through said holes.

* * * * *